United States Patent [19]

Hobbs et al.

[11] 4,204,997
[45] May 27, 1980

[54] ASYMMETRIC AMINATION OF 1,3-DIENES

[75] Inventors: Charles F. Hobbs, Des Peres; Dudley E. McMackins, St. Charles, both of Mo.

[73] Assignee: Monsanto Company, St. Louis, Mo.

[21] Appl. No.: 21,387

[22] Filed: Mar. 19, 1979

[51] Int. Cl.$^2$ .................... C07D 207/06; C07C 85/18
[52] U.S. Cl. .............................. 260/326.8; 252/431 P; 260/563 R; 260/563 C; 260/563 P; 260/574; 260/576; 260/577; 260/583 H; 260/584 B; 544/178; 544/403; 544/404; 546/184; 546/192
[58] Field of Search ................ 260/583 H, 577, 326.8; 252/431 P

[56] References Cited

U.S. PATENT DOCUMENTS

| | | | |
|---|---|---|---|
| 4,008,281 | 2/1977 | Knowles et al. | 260/606.5 P |
| 4,120,901 | 10/1978 | Hobbs et al. | 260/585 D |

OTHER PUBLICATIONS

Dzhemilev et al., "IZV. AKAD. NAUK SSSR, SER. KHIM", No. 10, pp. 2379-2380 (1975).

*Primary Examiner*—John Doll
*Attorney, Agent, or Firm*—Scott J. Meyer; James W. Williams, Jr.

[57] ABSTRACT

A process for the asymmetric synthesis of amines which comprises the amination of a conjugated diene having from 4 to about 20 carbon atoms in the presence of a catalyst system comprising a palladium compound and an optically active phosphine ligand containing at least two phosphorus atoms.

14 Claims, No Drawings

ASYMMETRIC AMINATION OF 1,3-DIENES

This invention relates to the asymmetric amination of conjugated dienes.

Many organic amines which are useful as pharmaceuticals, fungistats, herbicides and other biologically active agents exhibit chirality. That is, they contain an asymmetric carbon and can exist in two optically active forms or enantiomers. The biological activity of many of these compounds frequently has been shown to reside preponderantly or almost exclusively in one enantiomer. For example, the amine L-α-methyl-3,4-dihydroxyphenylalanine (methyldopa) is an important antihypertensive drug, whereas the D-isomer is completely inactive as a hypotensive agent.

With certain synthetic amine analgesics such as methadone and its derivatives, the levo-isomers exhibit significantly greater analgesic activity than the dextro-isomers; Eddy et al, J. Pharmacol. Expt'l. Therap. 98, 121-37 (1950). Conversely, with certain dithienylalkenylamines the dextro-isomers were found to have substantially greater analgesic potency than the levo-isomers; Green, Brit. J. Pharmacol. 8, 2-9 (1953).

In the case of various amine fungistats, for example, 2-aminobutane, the l-isomer is described as being 100 times more fungistatic than the d-isomer; U.S. Pat. No. 3,522,030. Similarly, in the case of certain amine herbicides, for example, 2,6-dinitroaniline derivatives, the levorotatory (−) isomers are disclosed as being much more effective as herbicidal agents than the corresponding dextrorotatory (+) isomers; U.S. Pat. Nos. 3,920,742; 4,025,532.

Consequently, convenient methods of asymmetric synthesis of amines would be of much value for the production of biologically active compounds.

A variety of asymmetric synthetic schemes for the production of chiral molecules hwave been demonstrated heretofore. One particularly useful method is the catalytic hydrogenation of certain acylaminoacrylic acids to amino acid derivatives as disclosed in U.S. Pat. No. 4,008,281. This method employs a catalyst which contains a transition metal such as rhodium, iridium and ruthenium in combination with an optically active bis phosphine compound. Catalytic reactions such as this are particularly attractive for asymmetric synthesis in that only a small amount of the usually expensive chiral induction agent need be used.

Only a few catalytic reactions are known which form C-N bonds and are suitable for the asymmetric synthesis of amines. One such example, reported by Dzhemilev et al, Izv. Akad. Nauk SSSR, Ser. Khim. No. 10, pp. 2379-80 (1975), consists in the amination of butadiene with morpholine using a complex nickel-based, aluminum alkyl catalyst system with an optically active monodentate dimenthyl phenylphosphonite ligand.

DESCRIPTION OF THE INVENTION

Recently, in U.S. Pat. No. 4,120,901, the present inventors disclosed the use of a palladium based catalyst system and a multidentate phosphine ligand for the amination of conjugated dienes with ammonia. In accordance with the present invention, certain ligands of the aforesaid type which have an asymmetric center and are thus optically active, are selectively used in combination with a palladium compound for the asymmetric amination of conjugated dienes. Dextro- or levo-isomers, but not racemic mixtures, are used. Although this synthesis is generally applicable for reaction of dienes with ammonia, aliphatic, aryl and alkylaryl amines to produce optically active amine products, no asymmetric induction occurred in the reaction of 1,3-butadiene with morpholine. This failure to obtain asymmetric induction in the reaction with morpholine was observed in both attempts with two different optically active phosphine ligands. Thus, the palladium catalyst system with the optically active multidentate phosphine ligand appears to exhibit significantly different reactivity than the complex nickel-based, aluminum alkyl catalyst with the optically active monodentate phosphine ligand of Dzhemilev et al.

In the reaction of conjugated dienes and all amines tested with the present palladium catalyst and optically active multidentate phosphine ligand (with the sole exception of morpholine) asymmetric induction was obtained. For example, enantiomeric excesses of up to 14% were obtained with ammonia using dextrorotatory 2,3-O-isopropylidene-2,3-dihydroxy-1,4-bis(diphenylphosphino)butane while up to 15% enantiomeric excesses were obtained with isopropylamine and levorotatory 1,2-bis(o-anisylphenylphosphino)ethane. The former phosphino ligand contains two asymmetric carbon atoms whereas in the latter phosphino ligand two asymmetric phosphorus atoms are present. The wide applicability of the present invention is further illustrated by the amination of 1,3-cyclohexadiene with pyrrolidine in which selectivity to the desired chiral product, N-2-hexenyl amine, was 100%. It is thus believed that the present asymmetric synthesis of amines has general applicability in the reaction of amines and conjugated dienes.

In general, the amines which can be used for amination of the conjugated dienes include, for example, ammonia, primary alkyl- and aryl-amines and secondary dialkyl-, diaryl-, and alkylaryl-amines having from one to about 20 carbon atoms. Illustrative examples of these amines are methylamine, ethylamine, propylamine, isopropylamine, butylamine, hexylamine, octylamine, octadecylamine, cyclohexylamine, cyclopentylamine, adamantylamine, dimethylamine, diethylamine, dihexylamine, dioctylamine, N-methylcyclohexylamine, diethanolamine, pyrrolidine, piperidine, piperazine, aniline, and substituted anilines having substituents such as alkyl (e.g. methyl, butyl), alkoxy (e.g. methoxy, butoxy), nitro and halo (e.g. chloro, bromo), phenylenediamines, and N-phenylenediamines.

The conjugated dienes contemplated for use in this invention are 1,3-dienes which can be open chain or cyclic having from 4 to about 20 carbon atoms such as, for example, 1,3-butadiene, isoprene, 1,3-pentadiene, 2,4-hexadiene, 2,3-dimethylbutadiene, 1,3-cyclopentadiene, 1,3-cyclohexadiene, and 1,3-cyclooctadiene.

Any of the readily available palladium compounds can be used in the catalyst system of this invention and it is unnecessary to initially prepare a complex structure with the palladium. Thus, commercially available palladium salts such as the acetate, nitrate, cyanide, and acetylacetonate salts are eminently suitable. Of these, palladium acetate is preferred.

The optically active multidentate phosphine ligands used in this catalyst system can be alkyl-, aryl- and arylalkyl phosphines containing one or more optically active centers and two or more phosphorus atoms. These preferably have 2 to 4 phosphorus atoms. Illustrative examples of these ligands are:

(+)-2,3-O-isopropylidene-2,3-dihydroxy-1,4-bis(diphenylphosphino)butane,
(−)-1,2-bis(o-anisylphenylphosphino)ethane,
(+)-1,2-bis(o-anisylcyclohexylphosphino)ethane,
(−)-1,2-bis(o-anisylethylphosphino)ethane,
(−)-1,2-bis(o-anisylphenylphosphino)propane,
(−)-1,2-bis(o-anisylphenylphosphino)butane,
(−)-1,2-bis(o-anisylphenylphosphino)ethylene,
(S,S)-2,3 butanediyl bis(diphenylphosphine),
(+)-1,2-bis(diphenylphosphino)propane,
(−)-4,5-bis(diphenylphosphinomethyl)-2,2-diphenyl-1,3-dioxolane,
(+)-O-isopropylidene-2,3-dihydroxy-1,4-bis[m-(α,αα,trifluorotolyl)phosphino]butane,
(R,R)-trans-4,5-bis(di-1-naphthalenylphosphinomethyl)-2,2-dimethyl-1,3-dioxolane,
(R,R)-trans-4,5-bis(di-2-naphthalenylphosphinomethyl)-2,2-dimethyl-1,3-dioxolane,
(R,R)-trans-4,5-bis(dimethylphenoxaphosphinomethyl)-2,2-dimethyl-1,3-dioxolane,
(R,R)-trans-4,5-bis(5H-dibenzophospholylmethyl)-2,2-dimethyl-1,3-dioxolane,
(+)-O-isopropylidene-2,3-dihydroxy-1,4-bis(di-m-tolylphosphino)butane,
(+)-O-isopropylidene-2,3-dihydroxy-1,4-bis(di-o-tolylphosphino)butane,
(+)-O-isopropylidene-2,3-dihydroxy-1,4-bis(di-p-tolylphosphino)butane.
(R,R)-1,2-bis(diphenylphosphinomethyl)cyclopentane,
(R,R)-trans-4,5-bis(diphenylphosphinomethyl)-2,2-pentamethylene-1,3-dioxolane,
(R,R)-trans-4,5-bis(diphenylphosphinomethyl)-2-phenyl-1,3-dioxolane,
(R,R)-2,3-bis(diphenylphosphinomethyl)-(2.2.2)bicyclo-octane,
(2S,4S)N-butoxycarbonyl-1-diphenylphosphino-2-diphenylphosphinomethyl pyrrolidine,
(2R,4R)-2,4-bis(diphenylphosphinomethyl)-1,3-dioxolane,
(2R,4R)N-phenylcarbonyl-1-diphenylphosphino-2-diphenylphosphinomethyl pyrrolidine,
N,N'-bis(S(−)α-methylbenzyl)ethylene diamine,
(+)-N-N'-bis(3-methylpinan-(11)-yl-N,N'-bis(diphenylphosphino)diaminoethane,
(+)-1,2-bis(diphenylphosphinomethyl)cyclobutane,
(+)-1,2-bis(dibenzylphosphinomethyl)cyclobutane,
(+)-1,2-bis(diethylphosphinomethyl)cyclobutane,
(−)-2,2'-bis(diphenylphosphinomethyl)-1,1'-binaphthyl,
N,N'-bis(S(−)α-methylbenzil)N,N'-bis(diphenylphosphino)-ethane,
(+)-1,2-bis(di-1-naphthalenylphosphino)ethane,
(+)-1,2-bis(di-1-napthalenylphosphino)butane,
(+)-1,2-bis(di-2-napthalenylphosphino)ethane,
(−)-1,2-bis(di-2-napthalenylphosphino)butane,
(+)-1,2-bis(di-o-tolylphosphino)ethane,
(+)-1,2-bis(di-o-tolylphosphino)butane,
(−)-1,2-bis(di-m-tolylphosphino)ethane,
(+),1,2-bis(di-m-tolylphosphino)butane,
(−)-1,2-bis(di-o-chlorophenylphosphino)ethane,
(−)-1,2-bis(di-m-chlorophenylphosphino)ethane.

It will be appreciated that opposite enantiomers of the foregoing compounds also are suitable for use in the present invention. For example, the levo-2,3-O-isopropylidene-2,3-dihydroxy-1,4-bis(diphenylphosphino)butane can be used in place of the above dextro-isomer and the dextro-1,2-bis(o-anisylphenylphosphino)ethane can be used in place of the above levo-isomer. Still other examples of suitable ligands will be readily apparent to the person skilled in the art by analogy to these exemplary compounds.

The reaction preferably is carried out in a hydroxylic solvent reaction medium. Suitable such solvents are methanol, ethanol, propanol, isopropanol, butanol, hexanol, cyclohexanol, octanol and decanol. Fluorinated solvents such as, for example, trifluoroacetic acid, can also be used in the reaction medium to increase the rate of reaction.

Reaction temperatures and reactant proportions can vary widely. Thus, the reaction temperature can range from about 0° to about 150° C., with the preferred range being from about 25° C. to about 100° C. The ratio of ammonia or amine to diene can vary from about 1:3 to about 24:1, with the preferred range being from about 1:2 to about 6:1. Reaction rates with cyclic amines and aniline generally were faster than with acyclic amines.

The ligand/palladium mole ratio generally will vary from about 1:10 to about 10:1, although the preferred ratio is about 1.4:1. The ratio of palladium compound to conjugated diene in the reaction can vary widely, with the preferred range being from about 1:10 to about 1:10,000.

The preferred products of the herein-defined asymmetric synthesis are the optically active 1-alkyl-2-enyl amines. The general structure of these products is:

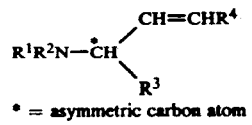

* = asymmetric carbon atom wherein $R^1$ and $R^2$ can be H, alkyl or aryl radicals having from one to about 20 carbon atoms;
$R^3$ can be an alkyl radical having from one to about 16 carbon atoms;
$R^4$ can be H or an alkyl radical having from one to about 16 carbon atoms; and
$R^3+R^4$ can have a total of from one to about 17 carbon atoms.

As examples of the above, the preferred product obtained from the reaction of 1,3-butadiene and diethylamine under the conditions described for this invention is:

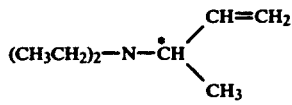

and the reaction of pyrrolidine with 1,3-cyclohexadiene in accordance with this invention gives

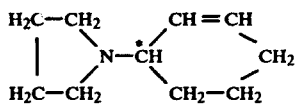

as the preferred product.

When open chain conjugated dienes are used as reactants in the described reaction, other amine co-products may be formed in varying amounts depending upon the specific reaction conditions selected. These co-products in the case where ammonia is used as the reacting amine, may be represented by the general structures:

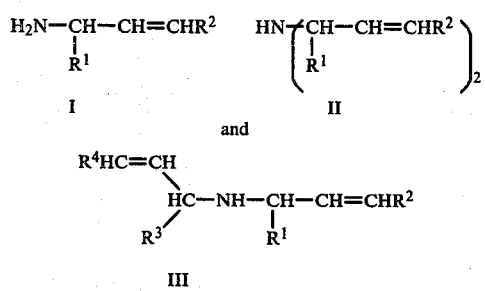

where $R^1-R^4$ may be hydrogen or alkyl radicals depending upon the structure of the diene reactant used. As examples, in the case where ammonia and 1,3-butadiene are used as the reactants in the invention, the above described co-products obtained are:

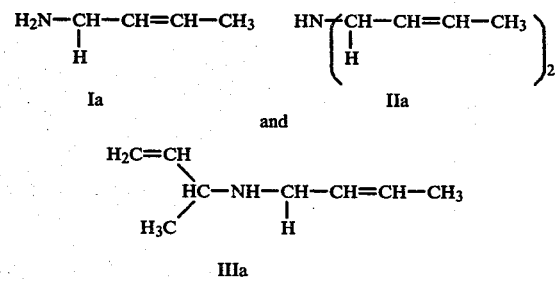

Smaller amounts of additional co-products representing several isomers of the general formula $C_{12}H_{21}N$ may also be formed under certain reaction conditions in the reaction of butadiene with ammonia.

In the case where primary or secondary amines and open chain conjugated dienes are used as reactants, the co-products which may be formed in varying amounts are represented by the general formulas:

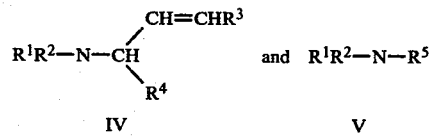

where $R^1$ is hydrogen, or an alkyl or aryl radical depending on the structure of the amine reactant used and where $R^2$ is an alkyl or aryl radical depending on the amine reactant, and where $R^3$ and $R^4$ are hydrogen or alkyl radicals depending upon the structure of the diene reactant used. $R^5$ represents an alkadienyl radical resulting from telomerization of two molecules of the diene reactant occurring during the amination reaction. These alkadiene radicals may be of two or more isomeric structures depending upon the structure of the diene reactant used. For example, in the case where isopropoylamine and 1,3-butadiene are used as reactants in this invention, the co-products obtained are:

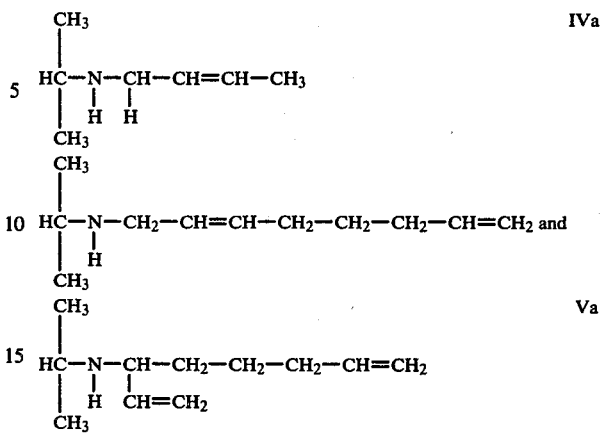

The preferred optically active amine products can be used directly or can be reduced to provide other optically active saturated amines. For example, the preferred α-methallylamine and its derivatives defined above can be readily hydrogenated to sec-butylamine [2-butylamine] or its derivatives. (−)-sec.Butylamine has shown good activity as a fungistat (U.S. Pat. No. 3,522,030) and derivatives of (−)-sec. butylamine have demonstrated activity as herbicides (U.S. Pat. Nos. 3,920,742 and 4,025,538).

The following detailed examples will further illustrate the invention although it should be understood that the invention is not limited to these specific examples.

EXAMPLE 1

1,3-Butadiene (0.27 mole), ammonia (1.6 mole), palladium acetate (1.9 mmole), (+)-2,3-O-isopropylidene-2,3-dihydroxy-1,4-bis(di-phenylphosphino)-butane (2.76 mmole) and n-butanol (16 ml) were heated in a 300 ml stainless steel reactor for 13.5 hr at 100° C. Analysis of the product showed 77% of the 1,3-butadiene had been converted to a mixture of α-methallylamine, 2-butenylamine, bis-(2-butenyl)-amine, and several isomers of amines of the general formulas $C_{12}H_{21}N$ and $C_{16}H_{27}N$. These products were present in the mole ratio of 27:20:42:11, respectively. The α-methallylamine product separated by distillation was shown to have 14% enantiomeric excess ($[\alpha]_D^{20} = +3.37°$) of the (+)-isomer.

EXAMPLE 2

When 1,3-cyclohexadiene (0.034 mole), pyrrolidine (0.18 mole), palladium acetate (0.24 mmole), (−)-1,2-bis-(o-anisylphenylphosphino)ethane (0.35 mmole), and methanol (2.5 ml) were heated for 65 hr at 80° C. 65% of the diene was converted to N-(2-cyclohexenyl)pyrrolidine, the only product. The product amine, isolated by distillation, exhibited the specific rotation, $[\alpha]_D^{20} = +11.8°$.

Various other examples were carried out in the manner of the foregoing examples with the specific reaction conditions and results being set forth in the following tables. The α-methallyl products were isolated, their optical rotation determined, and the enantiomeric excess (i.e. optical purity) calculated for those products whose absolute rotations were known or could be determined.

Enantiomeric excesses for α-methallylamine were determined using estimated absolute rotation values from the literature ($[α]_D^{20}=25.8°$) and confirmed by 270 mHz nmr determination of the relative amounts of the two enantiomers using the chiral shift reagent, tris-[3-(trifluoromethylhydroxymethylene)-d-camphorato] europium (III). For N-(2-methallyl)-i-propylamine, a value of $[α]_D^{20}=11.76°$ was used to calculate enantiomeric excess. Values for absolute rotations of the products for diethylamine, aniline, and pyrrolidine were not available and attempts to use the nmr chiral shift technique were unsuccessful in that no separation of peak was noted. Consequently, only specific rotations are shown for these cases.

Table 1

1,3-Butadiene + $NH_3$[a] + Pd(acetate)$_2$ + ligand + ROH

| Mole Ratio Charged | | | | Reaction Time, hr | Reaction Temp. °C. | Conversion to Amines, % Diene | Product Selectivity, Mole % | | |
|---|---|---|---|---|---|---|---|---|---|
| Amine/ Diene | Ligand/ Pd salt | Diene/ Pd salt | Ligand[b] | | | | $R^1R^2N\diagup\hspace{-1em}=$ | $R^1R^2NCH_2CH{:}CHCH_2$ | $R^1R^2NC_8H_{13}$ + $R^1R^2NC_{12}H_{19}$ + $R^1R^2NC_{16}H_{25}$ |
| 5.9 | 1.45 | 142 | (+)DIOP | 13.5 | 100 | 77 | 27 | 20 | 53 |
| 6.1 | 1.41 | 142 | (−)DIPAMP | 19 | 85 | 72 | 36 | 20 | 44[c] |

| | | | | | | | ROH | $[α]_D^{20}$ | α-methallyl Product % Enantiomeric Excess |
|---|---|---|---|---|---|---|---|---|---|
| | | | | | | | nBuOH | (+)3.37° | 14 |
| | | | | | | | nBuOH | (−)0.79° | 3 |

[a]$CF_3COONH_4$ added as a promoter (0.01 mole/mole Pd salt).
[b](−)DIPAMP = (−)-1,2-bis(o-anisylphenylphosphino)ethane. (+)DIOP = (+)-2,3-O-isopropylidine-2,3-dihydroxy-1,4-bis(diphenylphosphino)butane.
[c]With ammonia, the $C_8$ products are dibutenylamines $HN(C_4H_9)_2$.

Table 2

1,3-Butadiene + Diethylamine + Pd(acetate)$_2$ + ligand + ROH

| Mole Ratio Charged | | | | Reaction Time, hr | Reaction Temp. °C. | Conversion to Amines, % Diene | Product Selectivity, Mole % | | |
|---|---|---|---|---|---|---|---|---|---|
| Amine/ Diene | Ligand/ Pd salt | Diene/ Pd salt | Ligand[b] | | | | $R^1R^2N\diagup\hspace{-1em}=$ | $R^1R^2NCH_2CH{:}CHCH_2$ | $R^1R^2NC_8H_{13}$ + $R^1R^2NC_{12}H_{19}$ + $R^1R^2NC_{16}H_{25}$ |
| 5.9 | 1.42 | 144 | (+)DIOP | 17 | 100 | 75 | 2 | 16 | 83 |
| 5.9 | 2.86 | 144 | (+)DIOP | 245 | 60 | 100 | 2 | 94 | 2 |
| 6.9 | 1.42 | 123 | (+)DIOP | 17 | 60 | 72 | <0.5 | 7 | 93 |
| 5.9 | 1.42 | 144 | (−)DIPAMP | 17 | 80 | 86 | <0.5 | 79 | 17 |

| | | | | | | | ROH | $[α]_D^{20}$ | α-methallyl Product % Enantiomeric Excess |
|---|---|---|---|---|---|---|---|---|---|
| | | | | | | | ⬡S—OH | (−)0.46° | — |
| | | | | | | | MeOH | (−)0.20° | — |
| | | | | | | | MeOH | not isolated | — |
| | | | | | | | MeOH | 0.00 | — |

[b](−)DIPAMP = (−)-1,2-bis(o-anisylphenylphosphino)ethane. (+)DIOP = (+)-2,3-O-isopropylidine-2,3-dihydroxy-1,4-bis(diphenylphosphino)butane.

Table 3

1,3-Butadiene + Isopropylamine + Pd(acetate)$_2$ + ligand + ROH

| Mole Ratio Charged | | | | Reaction Time, hr | Reaction Temp. °C. | Conversion to Amines, % Diene | Product Selectivity, Mole % | | |
|---|---|---|---|---|---|---|---|---|---|
| Amine/ Diene | Ligand/ Pd salt | Diene/ Pd salt | Ligand[b] | | | | $R^1R^2N\diagup\hspace{-1em}=$ | $R^1R^2NCH_2CH{:}CHCH_2$ | $R^1R^2NC_8H_{13}$ + $R^1R^2NC_{12}H_{19}$ + $R^1R^2NC_{16}H_{25}$ |
| 5.9 | 1.42 | 144 | (+)DIOP | 18 | 100 | 82 | 13 | 11 | 76 |
| 5.9 | 1.42 | 144 | (−)DIPAMP | 19 | 80 | 86 | 21 | 22 | 57 |

| | | | | | | | ROH | $[α]_D^{20}$ | α-methallyl Product % Enantiomeric Excess |
|---|---|---|---|---|---|---|---|---|---|

Table 3-continued 1,3-Butadiene + Isopropylamine + Pd(acetate)$_2$ + ligand + ROH

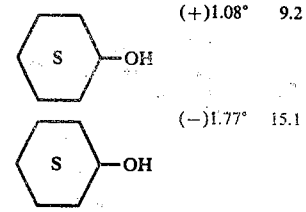

| | |
|---|---|
| (+)1.08° | 9.2 |
| (−)1.77° | 15.1 |

[b](−)DIPAMP = (−)-1,2-bis(o-anisylphenylphosphino)ethane. (+)DIOP = (+)-2,3-O-isopropylidine-2,3-dihydroxy-1,4-bis(diphenylphosphino)butane.

Table 4

1,3-Butadiene + Aniline + Pd(acetate)$_2$ + ligand + ROH

| Mole Ratio Charged | | | | Reaction Time, hr | Reaction Temp. °C. | Conversion to Amines, % Diene | Product Selectivity, Mole % | | | |
|---|---|---|---|---|---|---|---|---|---|---|
| Amine/ Diene | Ligand/ Pd salt | Diene/ Pd salt | Ligand | | | | $R^1R^2N\diagup\kern-1em=$ | | $R^1R^2NCH_1CH:CHCH_2$ | $R^1R^2NC_8H_{13}$ + $R^1R^2NC_{12}H_{19}$ + $R^1R^2NC_{16}H_{25}$ |
| 5.9 | 1.42 | 144 | (−)DIPAMP | 3 | 50 | 80 | 0 | | 0 | 100 |
| 5.9 | 1.42 | 144 | (+)DIOP | 2 | 50 | 99 | 12 | | 87 | 1 |

| | ROH | [α]$_D^{20}$ | α-methallyl Product % Enantiomeric Excess |
|---|---|---|---|
| | MeOH | — | — |
| | MeOH | (+)0.21° | — |

Table 5

1,3-Butadiene + Morpholine Pd(acetate)$_2$ + ligand + ROH

| Mole Ratio Charged | | | | Reaction Time, hr | Reaction Temp. °C. | Conversion to Amines, % Diene | Product Selectivity, Mole % | | |
|---|---|---|---|---|---|---|---|---|---|
| Amine/ Diene | Ligand/ Pd salt | Diene/ Pd salt | Ligand | | | | $R^1R^2N\diagup\kern-1em=$ | $R^1R^2NCH_1CH:CHCH_2$ | $R^1R^2NC_8H_{13}$ + $R^1R^2NC_{12}H_{19}$ + $R^1R^2NC_{16}H_{25}$ |
| 5.9 | 1.42 | 144 | (+)DIOP | 0.5 | 100 | 92 | 0.9 | 12 | 87 |
| 5.9 | 1.42 | 144 | (−)DIPAMP | 0.5 | 80 | 73 | 1.2 | 6 | 93 |

| | ROH | [α]$_D^{20}$ | α-methallyl Product % Enantiomeric Excess |
|---|---|---|---|
| | MeOH | 0.0° | — |
| | MeOH | 0.0° | — |

Table 6

1,3-Butadiene + Pyrrolidine + Pd(acetate)$_2$ + ligand + ROH

| Mole Ratio Charged | | | | Reaction Time, hr | Reaction Temp. °C. | Conversion to Amines, % Diene | Product Selectivity, Mole % | | |
|---|---|---|---|---|---|---|---|---|---|
| Amine/ Diene | Ligand/ Pd salt | Diene/ Pd salt | Ligand | | | | $R^1R^2N\diagup\kern-1em=$ | $R^1R^2NCH_1CH:CHCH_2$ | $R^1R^2NC_8H_{13}$ + $R^1R^2NC_{12}H_{19}$ + $R^1R^2NC_{16}H_{25}$ |
| 5.9 | 1.42 | 144 | (+)DIOP | 3 | 100 | 82 | 8 | 7 | 85 |
| 5.9 | 1.42 | 144 | (−)DIPAMP | 1 | 80 | 86 | 18 | 22 | 60 |
| 5.3 | 1.42 | 144 | (−)DIPAMP | 16 | 25 | 87 | 4 | 3 | 82 |

| | ROH | [α]$_D^{20}$ | α-methallyl Product % Enantiomeric Excess |
|---|---|---|---|
| | MeOH | (−)0.29° | — |
| | MeOH | (+)0.84° | — |
| | MeOH | (+)1.03° | — |

Table 7

| | | | | | | | 1,3-Cyclohexadiene + Pyrrolidine + Pd(acetate)$_2$ + ligand + ROH | | |
|---|---|---|---|---|---|---|---|---|---|
| | | | | | | | | Product Selectivity, Mole % | |
| | Mole Ratio Charged | | | Reaction Time, hr | Reaction Temp. °C. | Conversion to Amines, % Diene | R$^1$R$^2$N— 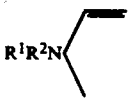 | R$^1$R$^2$NCH$_2$CH:CHCH$_2$ | R$^1$R$^2$NC$_8$H$_{13}$ + R$^1$R$^2$NC$_{12}$H$_{19}$ + R$^1$R$^2$NC$_{16}$H$_{25}$ |
| Amine/ Diene | Ligand/ Pd salt | Diene/ Pd salt | Ligand | | | | | | |
| 5.3 | 1.42 | 144 | (−)DIPAMP | 44 | 80 | 65 | 100 | — | — |

| | | | α-methallyl Product | |
|---|---|---|---|---|
| | | ROH | [α]$_D^{20}$ | % Enantiomeric Excess |
| | | MeOH | (+)11.8° | — |

Various other examples will be apparent to the person skilled in the art after reading this disclosure without departing from the spirit and scope of the invention. All such further examples are included within the scope of the appended claims.

What is claimed is:

1. A process for the asymmetric synthesis of amines which comprises amination of a conjugated diene having from 4 to about 20 carbon atoms in the presence of a catalyst system comprising a palladium compound and an optically active phosphine ligand containing at least two phosphorus atoms.

2. A process according to claim 1 wherein the amination employs an amine reactant selected from the group consisting of primary alkyl- and aryl-amines and secondary dialkyl-, diaryl-, and alkylaryl-amines having from one to about 20 carbon atoms.

3. A process according to claim 2 wherein the amine reactant is an alkylamine.

4. A process according to claim 2 wherein the amine reactant is isopropylamine.

5. A process according to claim 2 wherein the amine reactant is aniline.

6. A process according to claim 2 wherein the amine reactant is pyrrolidine.

7. A process according to claim 2 wherein the conjugated diene is 1,3-butadiene.

8. A process according to claim 2 wherein the conjugated diene is 1,3-cyclohexadiene.

9. A process according to claim 2 wherein the phosphine ligand contains from 2 to 4 phosphorus atoms.

10. A process according to claim 9 wherein the phosphine ligand is dextro- or levo-2,3-O-isopropylidene-2,3-dihydroxy-1,4-bis(diphenylphosphino)butane.

11. A process according to claim 9 wherein the phosphine ligand is dextro- or levo-1,2-bis(o-anisylphenylphosphino)ethane.

12. A process according to claim 11 wherein the amine reactant is pyrrolidine and the conjugated diene is 1,3-cyclohexadiene.

13. A process according to claim 2 wherein the amination is carried out in a solvent medium comprising a hydroxylic solvent.

14. A process according to claim 2 wherein the palladium compound is palladium acetate.

* * * * *